(12) United States Patent
Knox et al.

(10) Patent No.: US 6,184,537 B1
(45) Date of Patent: Feb. 6, 2001

(54) DETECTION OF AIRBORNE POLLUTANTS

(75) Inventors: Ronald Knox, Mornington; Christopher T. Ryan, East Brunswick, both of (AU)

(73) Assignee: Vision Products Pty Ltd. (AU)

( * ) Notice: Under 35 U.S.C. 154(b), the term of this patent shall be extended for 0 days.

(21) Appl. No.: 09/171,993

(22) Filed: Oct. 28, 1998

(30) Foreign Application Priority Data

May 3, 1996 (AU) .................................................. PN 9658

(51) Int. Cl.[7] .................................................. G08B 17/10
(52) U.S. Cl. ........................................ 250/574; 340/630
(58) Field of Search .................... 250/573, 574; 340/628, 630; 356/337, 338, 438, 439

(56) References Cited

U.S. PATENT DOCUMENTS 5,670,947 * 9/1997 Nagashima ........................... 250/574

FOREIGN PATENT DOCUMENTS

31841/84 2/1985 (AU) .

WO 89/09392 10/1989 (WO) .

OTHER PUBLICATIONS

Derwent Abstract Accession No. J079K/24, SU 949428, A, (Alkhazishvili RI) Aug. 7, 1982.

* cited by examiner

*Primary Examiner*—John R. Lee
*Assistant Examiner*—Kevin Pyo
(74) *Attorney, Agent, or Firm*—Wolf, Greenfield & Sacks, P.C.

(57) ABSTRACT

A smoke detector (2) which operates on the scattered light principle comprises a detector chamber (4) through which a light beam (10) passes. A series of collimator discs (24, 26, 28) with apertures of progressively increasing size are associated with the light source (6) to prevent glints of light from entering the zone of the chamber at which detection occurs as a result of the presence of scattered light induced by the presence of smoke particles. A light absorber (12) at the end of the detector chamber remote from the light source uses a target surface in the form of an asymmetric cone (42) onto which the beam is directed. The design of the collimator discs and light absorber reduce the occurrence of stray light, leading to increased sensitivity.

15 Claims, 2 Drawing Sheets

DETECTION OF AIRBORNE POLLUTANTS

FIELD OF THE INVENTION

The present invention relates to a device for the detection of airborne pollutants. More particularly the invention relates to a detector for smoke and other airborne pollutants as may be generated in the event of a fire or in circumstances which can lead to a fire.

BACKGROUND OF THE INVENTION

Fire protection and suppressant systems which operate by detecting the presence of smoke and other airborne pollutants are well known. Upon a threshold level of smoke being detected, an alarm may be activated and operation of a fire suppressant system may be initiated. While the fire itself will cause damage, considerable damage can also be caused by operation of the fire suppression system and subsequent removal of the suppressant can be quite hazardous. Many traditional suppressants, such as halon, are also ozone depleting whereby this use is environmentally undesirable. A detection system which is sufficiently sensitive to detect an abnormal condition prior to the onset of a fire is very advantageous as it enables action to be taken at a very early stage before the onset of actual fire conditions. For example, when most substances are heated, even before heating occurs to a point at which a fire commences, emissions will be generated and if these can be detected by a very sensitive system, a warning provided at that very early stage may allow the problem to be detected and rectified, or the equipment turned off, before the fire actually starts.

It is also desirable for the detection system to have a wide dynamic range of operation whereby it is effective not only at low levels of smoke and other airborne pollutants as may be generated prior to the onset of actual fire conditions as discussed above, but also is able to detect a range of higher threshold levels of smoke and other pollutants. High levels of smoke will indicate a greater likelihood of there being a fire and the higher thresholds can trigger alarms to shut down air conditioning, close fire doors, call a fire fighting service, and eventually trigger a suppression system if the smoke level becomes sufficiently high.

It is known for detection systems to incorporate a sampling pipe network consisting of one or more sampling pipes with sampling holes installed at positions where smoke or pre-fire emissions can be collected. Air is drawn in through the sampling holes and along the pipe by means of an aspirator or fan and is directed through a detector at a remote location.

Although there are a number of different types of smoke detectors which can be used as the detector in a system as outlined above, one particularly suitable form of detector for use in such a system is an optical scatter detector which is able to provide good sensitivity at reasonable cost. Optical scatter detectors operate on the principle that smoke particles or other airborne pollutants of small size when introduced into a detection chamber having a high intensity light beam will cause light scatter. The scattered light is sensed by a scattered light detector. The greater the amount of smoke particles within the sample introduced into the detector chamber the greater will be the amount of light scatter. The scatter detector detects the amount of scattered light and hence is able to provide an output signal indicative of the amount of smoke particles or other pollutant particles within the sample flow.

SUMMARY OF THE INVENTION

An objective of the present invention is to provide a smoke detector of optical scatter type having improved sensitivity to the presence of smaller amounts of smoke and other pollutants, and in particular to the presence of relatively small quantities of such pollutants as may be generated prior to the onset of actual fire conditions.

A significant factor affecting the sensitivity of a detector of optical scatter type is the amount of background light within the detector chamber. In particular, if very low levels of light scatter are to be detected as will occur when very small amounts of smoke or other pollutant particles are within the sample airflow through the chamber, the background light level must be very low. Although various electronic techniques can be used to improve the signal to noise ratio of the output signal from the detector, these techniques are all limited by the background light level within the detector.

The present invention relates to various aspects of detailed design of a detector which operates on the optical scatter principle, in order to reduce the background light level within the detector and thereby improve the sensitivity of the detector and the signal to noise ratio of the output.

According to one aspect of the present invention there is provided a smoke detector comprising a detector chamber, an inlet for introducing an airflow to be sampled into the chamber, an outlet for said airflow from the chamber, means for generating a beam of light within the chamber, a scattered light detector responsive to the presence of scattered light within a zone of the chamber consequent on the presence of smoke particles within the sampled airflow in said zone, a light absorber at an end of the chamber remote from the light source for receiving and absorbing said beam after passage through the chamber, first collimator means for collimating the beam, and second collimator means beyond the first collimator means, said second collimator means comprising a collimator disc having an aperture of a size such that the beam collimated by the first collimator means passes through the aperture in the disc without contacting the edge of the aperture, said disc serving to trap glints of light arising from the first collimator means to thereby reduce stray light in the said zone at which detection of light scatter occurs, said zone being beyond the second collimator means.

Advantageously, the first collimator means comprises a collimator disc (a first collimator disc) the aperture of which is preferably smaller than the aperture of the disc of the second collimator means (the second collimator disc), the second disc serving to trap glints of light arising from the edge of the aperture of the first disc.

Advantageously a third collimator disk is positioned beyond the second disk and with an aperture size such that the collimated beam passing through the aperture in the second disk also passes through the aperture in the third disk without touching the sides of the aperture, the third disk serving to trap at least the significant majority of glints of light which might happen to pass beyond the second disk whereby to prevent such glints from reaching the zone at which detection of light scatter takes place.

Advantageously the first and second disks are located as close to the light source as practicable and the third disk is placed as close to the detection zone as practicable, for example closely adjacent to the inlet for the sampled air.

Further according to the present invention, there is provided a smoke detector having a detector chamber, an inlet for introducing an airflow to be sampled into the chamber, an outlet for said airflow from the chamber, means for generating a beam of light within the chamber, a scattered light detector responsive to the presence of scattered light within the chamber consequent on the presence of smoke particles within the sampled airflow, and a light absorber at an end of the chamber remote from the light source for receiving and absorbing the beam after passage through the chamber, said detector further comprising a series of collimator discs with apertures of progressively increasing size associated with the light source to prevent glints of light from entering the zone of the chamber at which detection occurs as a result of the presence of scattered light induced by the presence of smoke particles.

According to another aspect of the invention there is provided a smoke detector having a detector chamber, an inlet for introducing an airflow to be sampled into the chamber, an outlet for said airflow from the chamber, means for generating a beam of light within the chamber, a scattered light detector responsive to the presence of scattered light within the chamber consequent on the presence of smoke particles within the sampled airflow, and a light absorber at an end of the chamber remote from the light source for receiving and absorbing the beam after passage through the chamber, wherein the light absorber comprises an enclosure with an entry port through which the beam enters the enclosure and with an internal boundary surface having an axis coincident with the axis of the beam, said enclosure having a target surface operative to deflect the incoming beam onto the boundary surface of the enclosure for absorption and reflection within the enclosure, said target surface being defined by part of the surface of a cone the tip of which is directed towards the entry port, and the axis of the cone being inclined relative to the axis of the beam.

In a preferred embodiment of the invention the centre of the base of the cone is substantially coincident with the axis of the beam whereby the cone is not in the form of a right circular cone. Preferably the boundary surface of the enclosure is double frusto-conical form which initially widens in diameter in a direction away from the entry port and then narrows in diameter, the axis of the double frusto-conical surface being substantially coincident with the axis of the beam.

A particularly preferred embodiment of the invention comprises a collimator disk arrangement and a light absorber as defined above.

BRIEF DESCRIPTION OF THE DRAWINGS

Embodiments of the invention will now be described by way of example only with reference to the accompanying drawings in which.

DETAILED DESCRIPTION

Figure 1:
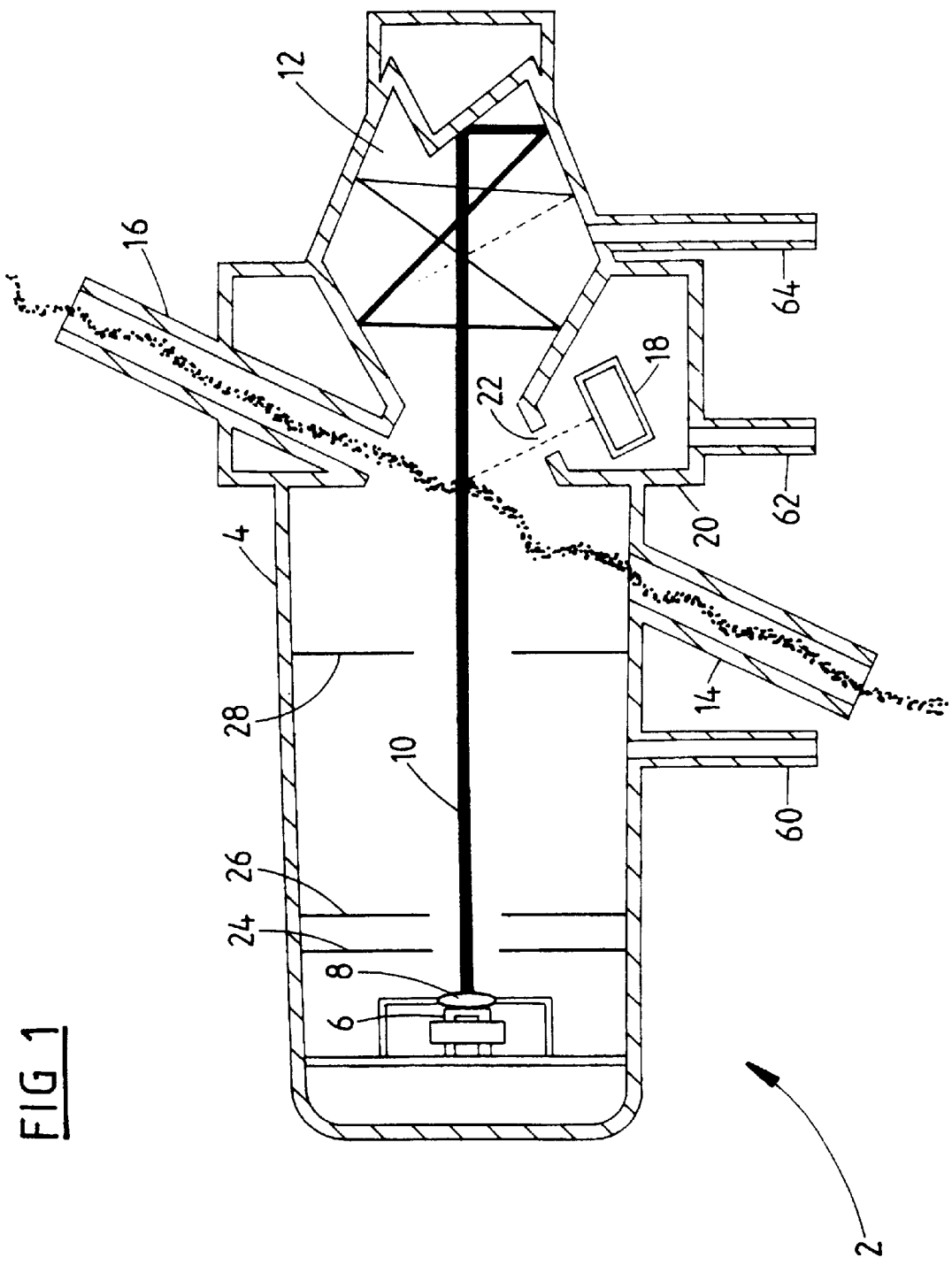
FIG. 1 is a schematic section through the detection chamber of a preferred embodiment of a smoke detector in accordance with the invention.

As shown in FIG. 1, a smoke detector 2 of optical scatter type comprises a detector chamber 4 of tubular form having at one end a light source 6 and lens 8 to produce a focussed beam 10 of light axially of the chamber 4. The light source 6 may either be a broad band source or a narrow band source. Examples of broad band sources are incandescent light bulbs, arc lamps and xenon flash lamps. Examples of narrow band light sources are filtered broad band light, LEDs and LASERS. The light source 6 in the detector of the preferred embodiment of the invention is a LASER although other forms of light source may alternatively be used. The light beam 10 is directed into a light absorber 12 at the other end of the chamber 4. The light beam entering the absorber 12 is subject to multiple reflections and absorption within the absorber 12 so that it does not re-enter the chamber 4. An inlet 14 and outlet 16 are provided for the airflow to be sampled so as to direct the airflow obliquely across the chamber 4 through the path of the beam 10 at a position adjacent the light absorber 12. A photo detector 18 for receiving scattered light is mounted within an enclosure 20 adjacent the absorber 12, the enclosure 20 having an entry port 22. A set of collimator disks 24, 26, 28 is provided to reduce stray light off the main axis.

It is to be noted that more than one photo detector can be incorporated to receive scattered light. The respective detectors may be in different locations within the chamber 4 and/or of different types.

The reduction in background light level and hence improved sensitivity in the detector of the preferred embodiment is achieved as a result of the configuration of the collimator disks and the design of the light absorber as will now be described.

In a collimator arrangement comprising a series of several disks uniformly spaced and with apertures of identical size, while this results in a removal of off-axis stray light, light contacting the edge of the aperture in the final disk of the series will result in glints of light beyond that disk and which, in turn, results in an increase in the background light level. Such an arrangement therefore limits the ratio of on-axis to off-axis light and sets a limit to the level to which the background light can drop. In the collimator arrangement of the preferred embodiment the three collimator disks 24, 26, 28 have apertures of different sizes, with the aperture of the second disk 26 being larger than that of the disk 24, and the aperture of the third disk 28 being larger than that of the disk 26. The first and second disks 24, 26 are relatively closely spaced and are positioned adjacent to the light source 6, and the third disk 28 is positioned a substantial distance away from the first and second disks 24, 26.

Figure 2:
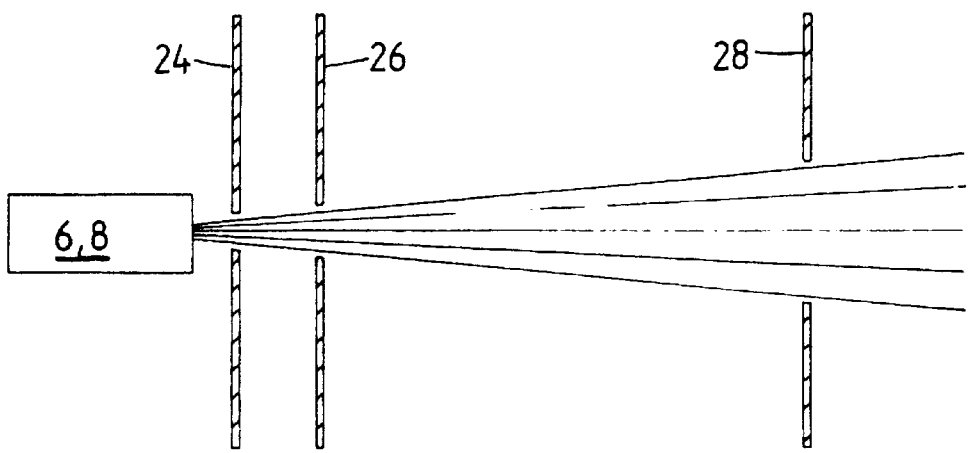
FIG. 2 shows schematically, and in exaggerated form, the arrangement of collimator disks within the detector.
Figure 3:
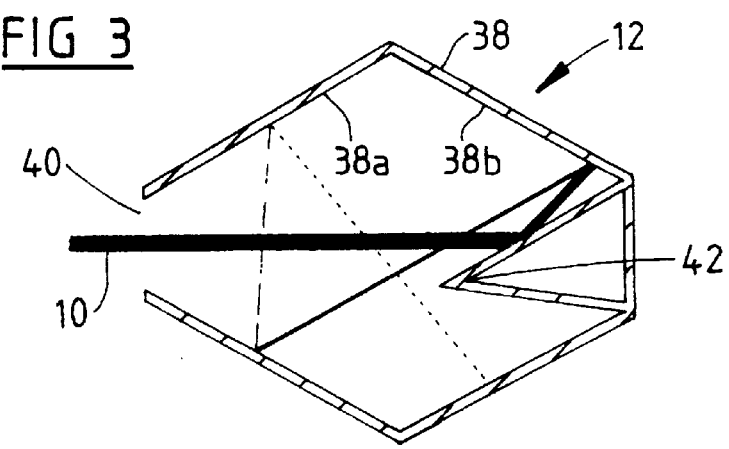
FIG. 3 is an axial section showing, schematically, a light absorber of the detector.
Figure 4:
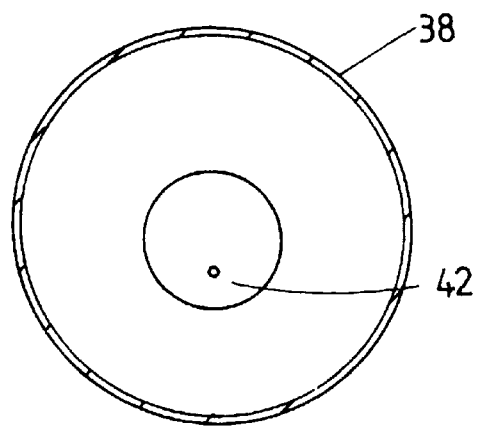
FIG. 4 is a schematic end elevation of the absorber as viewed from the front.

The disks 24, 26, 28 and the manner in which they co-operate with the light beam 10 are shown in an exaggerated schematic form in FIG. 2. With this arrangement it is the first disk 24 which provides the primary collimating effect on the light beam 10. The second disk 26 has an aperture of a size such that the collimated light beam 10 is able to pass through the aperture without contacting the edge of the aperture and consequently no glints will arise as a result of the passage of the light beam through the aperture of the second disk 26. The function of the second disk 26 is to trap the glints arising from the edge of the aperture in the first disk 24. The size of the aperture in the third disk 28 is larger than that in the second disk 26 whereby the light beam 10 will pass through the third disk 28 without contacting the edge of the aperture and, accordingly, without causing any further glints. Although the second disk 26 will trap the overwhelming majority of glints from the first disk 24 there is a possibility that some glints will pass through the aperture in the second disk 26 or reflect off the edge of the aperture in the second disk 26 towards the third disk 28. The third disk 28 thus serves to trap any glints passing via the second disk 26, or at least the significant majority of such glints. For maximum effectiveness, the third disk 28 is located as far away from the light source as is practicable and in practice this means it is as close to the sampling air inlet 14 into the chamber 4 as is practicable whereby the probability of any glints passing beyond the third disk 28 into the critical part of the chamber 4, in which light scatter is detected as a result of particles within the sample flow, is extremely remote. This results in a significant reduction in the background light level as a result of stray light and hence permits a substantial improvement in signal to noise ratio.

In a practical embodiment of the invention, where the light source 6 is a LASER diode used with a lens 8. this produces a collimated beam, but with off-axis stray light $10^5$ times higher than is desired. The three collimator discs 24, 26, 28 are used to reduce this off-axis stray light. In this practical embodiment, the diameter of the aperture in the first disc 24 is 3.5 mm, the diameter of the aperture in the second disk 26 is 4.0 mm, and the diameter of the aperture in the third disk 28 is 4.5 mm.

Although in the embodiment described, primary collimation of the beam is provided by the lens 8 and a single first disk 24, with the second and third disks 26, 28 serving to trap any stray light and glints arising from the first disk 24, in alternative arrangements primary collimation may be achieved by a lens and/or a first series of disks having apertures of identical size, followed by second and third disks as described herein.

The light absorber 12 at the end of the chamber 4 remote from the light source is used to absorb the light beam 10 after passage through the sample airflow. This is necessary as, otherwise, the beam 10 would be reflected thereby producing a level of background light that would swamp the relatively small amount of scattered light produced by smoke particles within the sample. The light absorber 12 comprises an enclosure 38 having an entry port 40 through which the beam 10 passes into the enclosure 38. The interior surface of the enclosure 38 is preferably defined by a smoothly polished black material in order to provide maximum absorption of light impinging on the surface without producing any diffuse reflections. As shown, the interior surface is of a double frusto-conical shape which first widens (38a) and then narrows (38b) with increasing distance away from the light source, the axis of this double frusto-conical surface being coincident with the axis of the light beam 10. The remote end of the absorber facing the entry port 40 carries a target surface 42 of generally conical form, the target surface 42 likewise preferably being composed of a smoothly polished black material. The light beam 10 enters the absorber 12 enclosure via the entry port 40 and strikes the generally conical target surface 42. Light reflected from the target surface 42 is subject to multiple reflection and absorption on the double frusto-conical surface 38a, 38b of the enclosure 38.

When the target surface 42 is in the form of a right circular cone, the axis of which is aligned with the axis of the beam 10 the conical tip portion of the surface will reflect the beam in a circular pattern. However, in practice it is extremely difficult to construct a perfect cone and to ensure that its tip is precisely aligned on the axis of the beam and as a result what occurs in practice is that the reflection pattern is not totally predictable and will vary from detector to detector and this variability can result in some stray light exiting from the absorber through the entry port 40.

In order to avoid this difficulty the light absorber 12 does not use a target surface 42 in the form of a right circular cone but, rather, it uses a cone of asymmetric form with the main axis of the cone from the centre of the base to the tip of the cone being inclined to an axis extending perpendicularly through the centre of the base of the cone, with this latter axis being coincident with the axis of the beam. As a result of this inclination, the beam 10 entering the absorber will engage the conical surface of the target at a predetermined position along the length of the surface (rather than at or adjacent the conical tip as occurs if a right circular conical target surface is used) and this enables a significantly more predictable reflection pattern to be achieved. It is to be noted that slight variations which might arise from sample to sample will not result in significant variation in the reflection pattern which occurs within the absorber whereby the geometry of the absorber surfaces can be designed to provide total absorption of light within the absorber substantially without the possibility of stray light exiting the absorber, this effect being repeatable from sample to sample notwithstanding slight variations which might arise during manufacture of the absorber and assembly and set up of the detector system. Accordingly, there is not a requirement for high precision in the manufacture of the absorber whereby a satisfactory absorber can be produced at substantially reduced cost.

In a practical embodiment of the invention the angle at which the axis of the cone is inclined to the perpendicular axis is about 15 degrees which is sufficient to ensure that no part of the beam shines on the tip of the cone. When the light source is a plain polarised light source it is preferred for the inclination to be within the plane of polarisation because this increases the absorption of light incident on the surface and less light is reflected.

Although in the detector described, the arrangement of collimator disks and the design of the light absorber both contribute to a low background light level, the collimator arrangement described will still have beneficial effect in reducing light level when the detector incorporates another form of light absorber, and the described light absorber will lead to a reduction in background light level without the presence of the described collimator arrangement.

In a smoke detector which operates on the optical scatter principle, smoke particles and small dust particles present within the sample air can, over a period of time, settle on and contaminate critical parts of the optical system such as the surface of the scattered light detector and other optical components of the system thereby reducing the sensitivity of the system. However the detector of the preferred embodiment of the invention has provision for ultra-filtered clean air (for example, air from which all particles in excess of approximately 0.3 microns have been removed by filtration) to be introduced into the detection chamber at selected positions to prevent the accumulation of smoke particles or other small particles on critical parts of the detector.

Inlets through which clean air is bled into the chamber 4 are shown at 60, 62, 64. Clean air entering through the inlet 60 into the zone of the chamber 4 between the second and third collimator discs 26, 28 serves to direct the sampling air away from the LASER and lens assembly 6, 8. Clean air from the inlet 62 enters the detector enclosure 20 and flows out of the enclosure 20 via the entry port 22 and thereby prevents the sampling air from entering into the enclosure 20 and hence contaminating the light scatter detector 18. Finally, the inlet 64 directs clean air into the light absorber 12, to prevent sample air from entering the absorber and contaminating the optical surfaces of the absorber. The clean air is drawn from the zone between the collimator discs 26, 28, the detector enclosure 20 and the light absorber 12 into the outlet 16 via the interior of the chamber 4. Accordingly, contamination of the surfaces of these optical devices with smoke and other small sized particles with commensurate reduction in the sensitivity of the system is thereby prevented.

The embodiment has been described by way of example only and modifications are possible within the scope of the invention.

What is claimed is:

1. A smoke detector comprising a detector chamber, an inlet for introducing an airflow to be sampled into the chamber, an outlet for said airflow from the chamber, means for generating a beam of light within the chamber, a scattered light detector responsive to the presence of scattered light within a zone of the chamber consequent on the presence of smoke particles within the sampled airflow in said zone, a light absorber at an end of the chamber remote from the light source for receiving and absorbing said beam after passage through the chamber, first collimator means for collimating the beam, and second collimator means beyond the first collimator means, said second collimator means comprising a collimator disc having an aperture of a size such that the beam collimated by the first collimator means passes through the aperture in the disc without contacting the edge of the aperture, said disc serving to trap glints of light arising from the first collimator means to thereby reduce stray light in the said zone at which detection of light scatter occurs, said zone being beyond the second collimator means.

2. A smoke detector according to claim 1, wherein the first collimator means comprises a collimator disc, and the disc of the second collimator means serves to trap glints of light arising from the edge of the disc of the first collimator means.

3. A smoke detector according to claim 1, comprising a further collimator disc positioned beyond the disc of the second collimator means and with an aperture size such that the collimated beam passing through the aperture in the disc of the second collimator means also passes through the aperture in the further disc without touching the sides of the aperture, the further disc serving to trap at least the significant majority of glints of light which might happen to pass beyond the disc of the second collimator means whereby to prevent such glints from reaching the said zone at which detection of light scatter takes place, said zone being beyond the further disc.

4. A smoke detector according to claim 3, wherein the first and second collimator means are located adjacent to the light source and the said further disc is adjacent to the detection zone.

5. A smoke detector according to claim 3, wherein the aperture of the said further collimator disc is of larger size than the aperture of the disc of the second collimator means.

6. A smoke detector according to claim 3, wherein the inlet for introducing the sampling airflow into the chamber leads into the detection zone of the chamber at a position closely adjacent the said further disc.

7. A smoke detector according to claim 1, wherein the detector comprises at least one inlet for admitting ultra-filtered clean air into the chamber to prevent the accumulation of particulate matter on parts of the detector the contamination of which would reduce the sensitivity of the detector.

8. A smoke detector according to claim 7, wherein said inlet for admitting ultra-filtered clean air into the chamber is positioned to direct sampling air away from the means for generating the beam of light.

9. A smoke detector according to claim 7, wherein said inlet for admitting ultra-filtered clean air into the chamber is positioned to admit the air into an enclosure for the scattered light detector to prevent sampling air from entering into the enclosure and contaminating the detector.

10. A smoke detector according to claim 1, wherein the light absorber comprises an enclosure with an entry port through which the beam enters the enclosure and with an internal boundary surface, said enclosure having a target surface operative to deflect the incoming beam onto the boundary surface of the enclosure for absorption and reflection within the enclosure, said target surface being defined by part of the surface of a cone the tip of which is directed towards the entry port, the axis of the cone being inclined relative to the axis of the beam.

11. A smoke detector according to the claim 10, wherein the centre of the base of the cone is substantially coincident with the axis of the beam.

12. A smoke detector according to claim 10, wherein the boundary surface of the enclosure is of double frustro-conical form which initially widens in diameter in a direction away from the entry port and then narrows in diameter.

13. A smoke detector according to claim 10, comprising an inlet for admitting ultra-filtered clean air into the light absorber to prevent sampling air from entering into the absorber and contaminating optical surfaces of the absorber.

14. A smoke detector having a detector chamber, an inlet for introducing an airflow to be sampled into the chamber, an outlet for said airflow from the chamber, means for generating a beam of light within the chamber, a scattered light detector responsive to the presence of scattered light within the chamber consequent on the presence of smoke particles within the sampled airflow, and a light absorber at an end of the chamber remote from the light source for receiving and absorbing the beam after passage through the chamber, said detector further comprising a series of collimator discs with apertures of progressively increasing size associated with the light source to prevent glints of light from entering the zone of the chamber at which detection occurs as a result of the presence of scattered light induced by the presence of smoke particles.

15. A smoke detector according to claim 14, wherein the light absorber comprises a target surface in the form of an asymmetric cone onto which the beam is directed.

* * * * *